(12) United States Patent
Parikh et al.

(10) Patent No.: US 8,153,159 B2
(45) Date of Patent: Apr. 10, 2012

(54) MODAFINIL MODIFIED RELEASE PHARMACEUTICAL COMPOSITIONS

(75) Inventors: Alpa Parikh, Avondale, PA (US); Piyush Patel, Wallingford, PA (US)

(73) Assignee: Cephalon, Inc., Frazer, PA (US)

( * ) Notice: Subject to any disclaimer, the term of this patent is extended or adjusted under 35 U.S.C. 154(b) by 1542 days.

(21) Appl. No.: 10/944,528

(22) Filed: Sep. 17, 2004

(65) Prior Publication Data

US 2005/0095294 A1    May 5, 2005

Related U.S. Application Data

(60) Provisional application No. 60/504,028, filed on Sep. 18, 2003.

(51) Int. Cl.
*A61K 31/165*    (2006.01)

(52) U.S. Cl. ........ 424/490; 424/451; 424/452; 424/468; 424/489; 424/497

(58) Field of Classification Search .................. 424/471, 424/464, 465, 489, 458, 474, 476, 490
See application file for complete search history.

(56) References Cited

U.S. PATENT DOCUMENTS

| | | | |
|---|---|---|---|
| 5,667,804 A * | 9/1997 | Wong et al. | 424/472 |
| 6,344,215 B1 | 2/2002 | Bettman et al. | |
| 6,346,548 B1 * | 2/2002 | Miller et al. | 514/618 |
| 2001/0038863 A1 | 11/2001 | Hanggi et al. | |
| 2001/0046964 A1 * | 11/2001 | Percel et al. | 514/29 |
| 2002/0099097 A1 * | 7/2002 | Jacobs et al. | 514/618 |
| 2003/0220403 A1 * | 11/2003 | Corvari et al. | 514/618 |

FOREIGN PATENT DOCUMENTS

| | | |
|---|---|---|
| WO | WO 01/87830 A2 | 11/2001 |
| WO | WO 02/056915 A2 | 7/2002 |
| WO | WO 02/096401 | 12/2002 |
| WO | WO 03/007919 A1 | 1/2003 |
| WO | WO 2004/024134 | 3/2004 |

OTHER PUBLICATIONS

Junginger, "VII Oral Applications of Pulsatile Drug Delivery", Pulsatile Drug Delivery Current Applications and Future Trends, Ed. 1, pp. 113-134, Wiss. Verlagsges., Stuttgart, 1993.

* cited by examiner

*Primary Examiner* — Michael G Hartley
*Assistant Examiner* — Micah-Paul Young

(57) ABSTRACT

Pharmaceutical compositions comprising modafinil. The pharmaceutical compositions can have a release profile which is different than that of traditional pharmaceutical compositions of modafinil.

22 Claims, 9 Drawing Sheets

MODAFINIL MODIFIED RELEASE PHARMACEUTICAL COMPOSITIONS

This application claims the benefit of U.S. Provisional Application No. 60/504,028 filed Sep. 18, 2003.

FIELD OF THE INVENTION

This invention relates to the acetamide derivative modafinil. Modafinil ($C_{15}H_{15}NO_2S$), is 2-(benzhydrylsulfinyl)acetamide, and is also known as 2-[(diphenylmethyl)sulfinyl] acetamide.

BACKGROUND OF THE INVENTION

1. Modafinil

Modafinil has been described as presenting a "neuropsychopharmacological spectrum characterized by the presence of excitation with hyperactivity and of hypermotility; and by the absence of stereotypy (except in high doses) and of potentialization of the effects of apomorphine and amphetamine" (U.S. Pat. No. 4,177,290; hereinafter "the '290 patent," which is incorporated herein by reference). A single administration of modafinil results in increased locomotor activity in mice and increased nocturnal activity in monkeys (Duteil et al., Eur. J. Pharmacol. 180:49 (1990)). The neuropsychopharmacological profile of modafinil has been distinguished from that of amphetamines (Saletu et al., Int. J. Clin. Pharm. Res. 9:183 (1989)). Modafinil is thought to modulate the central postsynaptic $alpha_1$-adrenergic receptor, without participation of the dopaminergic system (Duteil et al., supra). Modafinil has been successfully tested in humans for treatment of idiopathic hypersomnia and narcolepsy (Bastuji et al., Prog. Neuro-Psych. Biol. Psych. 12:695 (1988)).

Modafinil has been shown to be effective in treating narcolepsy, sleepiness, excessive sleepiness (e.g., sleepiness associated with disorders of sleep and wakefulness), excessive daytime sleepiness associated with narcolepsy, Parkinson's disease, urinary incontinence, multiple sclerosis fatigue, ADHD, Alzheimer's disorder, sleep apnea, obstructive sleep apnea, depression, and ischemia.

Narcolepsy is a chronic disorder characterized by intermittent sleep attacks, persistent, excessive daytime sleepiness and abnormal rapid eye movement ("REM") sleep manifestations, such as sleep-onset REM periods, cataplexy, sleep paralysis and hypnagogic hallucinations, or both (Assoc. of Sleep Disorders Centers, Sleep 2:1 (1979)). Most patients with narcolepsy also have disrupted nocturnal sleep (Montplaisir, in Guilleminault et al. eds., Narcolepsy, Spectrum Pub., New York, pp. 43-56). Pathological somnolence, whether due to narcolepsy or other causes, is disabling and potentially dangerous. Causes of pathological somnolence, other than narcolepsy, include chronic sleep loss (Carskadon et al., Sleep, 5:S73 (1982); Carskadon et al., Psychophysiology, 18:107 (1981)); sleep apnea (Kryger et al., Principles and Practice of Sleep Medicine, W. B. Saunders Co., Philadelphia, Pa. (1989)); and other sleep disorders (International Classification of Sleep Disorders: Diagnostic and Coding Manual, American Sleep Disorder Association, Rochester, Minn. (1990)). Whether due to narcolepsy or other causes, pathological somnolence produces episodes of unintended sleep, reduced attention, and performance errors. Consequently, it is linked to a variety of transportation and industrial accidents (Mitler et al., Sleep 11:100 (1988)). A therapeutic agent that reduces or eliminates pathological somnolence would have important implications not only for individual patients, but also for public health and safety.

Other uses of modafinil have been presented. U.S. Pat. No. 5,180,745 discloses the use of modafinil for providing a neuroprotective effect in humans, and in particular for the treatment of Parkinson's disease. The levorotatory form of modafinil, i.e., (−) benzhydrylsulfinyl-acetamide, may have potential benefit for treatment of depression, hypersomnia and Alzheimer's disease (U.S. Pat. No. 4,927,855). European Published Application 547952 (published Jun. 23, 1993) discloses the use of modafinil as an anti-ischemic agent. European Published Application 594507 (published Apr. 27, 1994) discloses the use of modafinil to treat urinary incontinence.

U.S. Pat. No. RE37,516 discloses pharmaceutical compositions having a defined particle size, and in particular compositions wherein 95% of the cumulative total of an effective amount of modafinil particles in the composition have a diameter less than about 200 microns.

Particles of modafinil can be formed via precipitation, granulation and milling or by extrusion/spheronization.

2. Alternative Dosage Forms: Generally

Control of delivery can be important when traditional oral or injectable formulations cannot be used. The features of controlled release may include, but are not limited to:

a. slow release of water-soluble drugs;
 b. fast release of low-solubility drugs;
 c. delivery to specific sites;
 d. delivery of two or more actives in the same formulation; and
 e. systems based on carriers that can dissolve or degrade and be readily eliminated.

Controlled drug delivery can also provide the following advantages:

a. eliminate over or underdosing;
 b. maintain drug levels in a desired range;
 c. reduce the need for repetitive dosing;
 d. increased patient compliance; and
 e. assist in the redirection or prevention of side effects.

Oral dosage forms are known which provide a zero order or first order release in which the drug is released at a substantially steady rate of release per unit of time. These dosage forms are satisfactory for the administration of pharmaceutical dosage forms of many drugs. Such dosage forms provide for an increase of blood levels of a drug that peaks and then begins to fall as the drug is metabolized or otherwise excreted.

However, in certain circumstances, more constant blood levels of a drug or multiple peaks are desirable. Such dosage forms which can provide such an effect are generally referred to as "Extended Release Dosage Forms." As used herein, extended release dosage forms that provide generally constant blood levels of a drug over time are referred to as "sustained release forms," and dosage forms that provide distinct blood level peaks of a drug over time are referred to as "pulsatile release forms." Both of these forms are described generally below.

A. Sustained Release Forms

A sustained release drug formulation is capable of providing immediate release of a drug, yet prolong the release of the drug such that the blood levels of the drug are maintained within a relatively narrow range over a period of time.

Sustained release drug formulations can be conventionally produced as compressed tablets, e.g., by hydrogel tablet technology. Among other alternatives, it is conventional in the drug industry to prepare encapsulated drug formulations which provide sustained release properties. In this situation, the sustained release capsule dosage forms may be formulated by mixing the drug with one or more binding agents to form a uniform mixture which is then moistened with water or a solvent such as ethanol to form an extrudable plastic mass from which small diameter, typically 1 mm, cylinders of drug/matrix are extruded, broken into appropriate lengths and transformed into spheroids using standard spheronization equipment. The spheroids, after drying, may then be film-coated to retard dissolution. The film-coated spheroids may then be placed in pharmaceutically acceptable capsules, such as starch or gelatin capsules, in the quantity needed to obtain the desired therapeutic effect. Spheroids releasing the drug at different rates may be combined in a capsule to obtain desired release rates and blood levels. U.S. Pat. No. 4,138,475 discloses an extended release pharmaceutical composition consisting of a hard gelatin capsule filled with film-coated spheroids comprised of propanol in admixture with microcrystalline cellulose wherein the film coating is composed of ethyl cellulose, optionally, with hydroxypropylmethylcellulose and/or a plasticizer.

B. Pulsatile Release Forms

As described above, an oral dosage form which provides a zero order or first order release in which a drug is released at a substantially steady rate of release per unit of time can be satisfactory for the administration of a drug in certain situations, depending on the needs of the subject.

However, in some instances, a pulsatile release form can be used to provide two or more dosings of a drug, typically with a predetermined period of time between each dose or at specific sites along the gastrointestinal tract, without the need for two or more oral administrations. However, there are only a few such orally applicable pulsatile release systems due to the potential limitation of the size or materials used for dosage forms.

The term "pulsatile release forms" (hereafter sometimes referred to as "pulsatile forms") is synonymous with the term "modulated delivery systems" and according to Peppas (N. A. Peppas, Preface in R. Gumy; H. E. Junginger; N. A. Peppas (Eds.) Pulsatile Drug Delivery, Current Applications and Future Trends, 1 Ed., page 5-5, Wiss. Verlagsges., Stuttgart 1993) designates a delivery system for medication which is capable of delivering the contained medical agent in prescribed intervals.

Until now, the preferred field of application of pulsatile forms of medication were illnesses such as ischemic heart disease, asthma, arthritis, avoiding developing a tolerance to nitrates, antibiotics and steroidal contraceptives, where absorption windows exist, HIV/AIDS, and states of pain (H. E. Junginger, Oral Applications of Pulsatile Drug Delivery in R. Gumy; H. E. Junginger; N. A. Peppas (Eds.) Pulsatile Drug Delivery, Current Applications and Future Trends, Ed. 1, pages 113-134, Wiss. Verlagsges., Stuttgart 1993). These illnesses or states of pain are subjected to time variations such that they can be treated best with forms of medication which are adapted with the intermittent (pulsatile) release of the medical agents to the occurrence of episodes of the illness or of attacks of the pain. Clearly, in such cases, a "time-controlled" pulsatile drug delivery system may be more advantageous. There are also instances in which a "position-controlled" drug delivery system (e.g. treatment of colon disease or use of colon as an absorption site for peptide and protein based products) may prove to be more efficacious.

Typical pulsatile forms of medication deliver the contained medical agent in one step (one pulse system), two steps (bimodal, double pulse system). In addition, however, more complicated systems and mixed systems have been described, which can possibly deliver the medical substances in several steps.

Junginger (H. E. Junginger, Oral Applications of Pulsatile Drug Delivery in R. Gumy; H. E. Junginger; N. A. Peppas (Eds.) Pulsatile Drug Delivery, Current Applications and Future Trends, Ed. 1., pages 113-134, Wiss. Verlagsges., Stuttgart 1993) gives examples for pulsatile forms of medication and recites in particular: coated tablets, pellets or microballs, osmotic systems, special capsules, time-controlled explosion systems, and special layer tablets.

3. Dosings of Modafinil

Typically, modafinil is administered in 100 mg and/or 200 mg doses once or twice daily to a person having a condition that is responsive to treatment by modafinil. Preferably, a single dose having an effective amount of modafinil is administered to the person upon waking. However, in some instances a second dose, also having an effective amount of modafinil, can be administered about six to twelve hours after the first dose in order to increase blood levels of modafinil to levels sufficient to continue to treat the condition or conditions that are responsive to modafinil.

With traditional dosings, it is desirous for blood levels of a drug to remain between a maximum blood level which may represent a toxic level and a minimum value below which the drug is no longer effective. However, maintenance of blood levels can be difficult. For example, traditional dosage forms can provide an erratic blood concentration profile. After administration of a first dose, blood levels can increase and exceed the maximum desired level, then drop off to levels below the minimum effective level before a second or subsequent dose is administered. The same cycle can be undesirably repeated with subsequent dosings of modafinil.

SUMMARY OF THE INVENTION

In one embodiment of the present invention, the blood level profile of a drug can be maintained above a minimum effective level and below a maximum desirable level over an extended period of time. Accordingly, in one embodiment, the present invention provides for a dosage form containing modafinil that can provide a sustained effect over a period of time, from about 6 to 12 hours.

In another embodiment of the present invention, a composition including, but not limited to, a pharmaceutical composition of modafinil having a release mechanism that differs from the release mechanism of Provigil® (modafinil), and provides a composition that is effective to alter the somnolent state of a subject, is described, as well as other neurological conditions that are treatable by modafinil, such as ADHD.

In one embodiment, the present invention includes a pharmaceutical composition in unit dose form, such that when administered, the unit dose form releases two or more effective amounts of modafinil, wherein the release of at least one of the effective amounts of modafinil is preceded by a time interval during which substantially no drug is released from the dosage form.

In another embodiment, the present invention includes a pharmaceutical composition in unit dose form, such that when administered, the unit dose form releases a first effective amount of modafinil, followed by a time interval during which substantially no drug is released from the dosage form, and after which time interval a second effective amount of modafinil is released from the pharmaceutical composition.

In another embodiment, the present invention includes a pharmaceutical composition in unit dose form, such that when administered, the unit dose form can immediately release an effective amount of modafinil, and also provides a second amount of modafinil that is released more slowly, wherein the release of the second amount of modafinil occurs over a given time interval, during which time the blood levels of modafinil are maintained at a generally constant level, typically at or above the minimum level necessary to be effective to treat a disease or condition that is responsive to modafinil.

In yet another embodiment, the present invention includes a method of altering the somnolent state of a mammal, such as a human, by administering to the mammal an effective amount of modafinil in an extended release dosage form of the present invention.

In yet another embodiment, the present invention includes a method of altering the somnolent state of a mammal, such as a human, by administering to the mammal an effective amount of the composition of the present invention.

DETAILED DESCRIPTION

Figure 1:
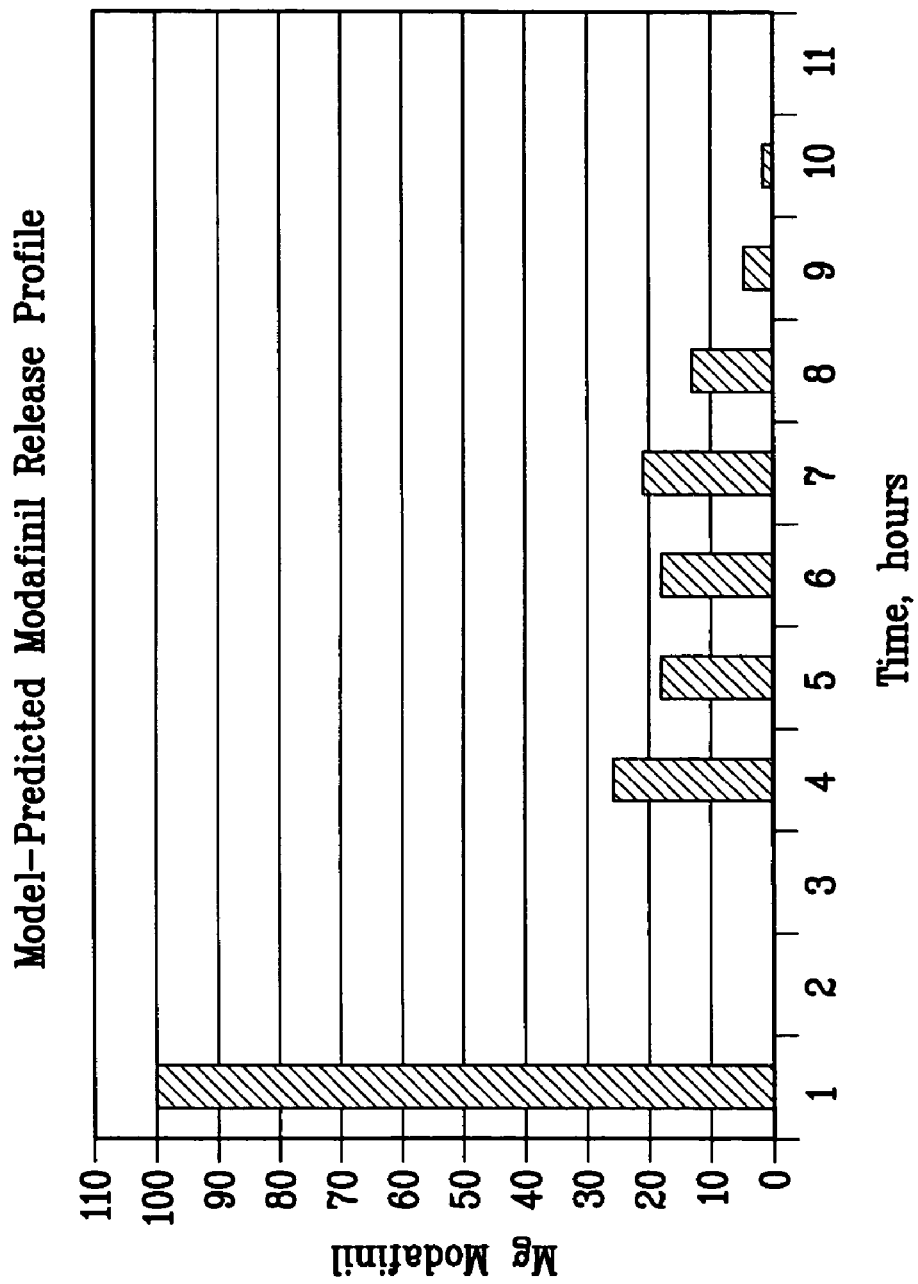
FIG. 1 shows a modafinil release profile of one embodiment of a delayed extended release dosage form of the present invention.

As disclosed herein and as used in the compositions and methods of the present invention, a modafinil compound can include a racemic mixture, and can optionally be in an acid form, such as a metabolic acid of modafinil or a benzhydryl-sulfinylacetic acid, a sulfone form, a hydroxylated form, a conjugated form such as a modafinil compound conjugated to a protein, a polysaccharide, a glucuronide or a sulfate, or a polymorphic form, it may include compounds containing isosteric replacements of the phenyl groups of modafinil, and polymorphic species or analogs of modafinil, enantiomers, or derivatives of cogeners and prodrugs. In preferred embodiments, the modafinil compound is a modafinil compound as contained in Provigil® (modafinil). However, it should be noted that other forms of modafinil can also be suitable for use in the present invention, e.g., a stabilized polymorph of modafinil which is bioequivalent to Provigil® (modafinil). Prodrugs are known in the art as compounds that are converted to the active agent (modafinil) in the body of a subject.

In accordance with the present invention, the modafinil can be provided in a modified release dosage form such as a pulsatile release dosage form and/or a sustained release dosage form, as described in more detail in the sections below.

Pulsatile Release Dosage Forms of Modafinil

In one embodiment, a pulsatile release form of modafinil of the present invention can include an active core of modafinil, having one or more coatings thereon, referred to herein as a "Coated Core of Modafinil." The coated core of modafinil can also be used in combination with an amount of modafinil suitable for immediate release, including but not limited to Provigil® (modafinil), as described below.

In another embodiment, the present invention can include an amount of modafinil suitable for immediate release in combination with at least a second amount of modafinil formulated such that the second amount of modafinil has a delay before onset and the release of the second portion of modafinil can be extended over time. Such an embodiment is referred to herein as "Delayed Extended Release of Modafinil." Each of the pulsatile release dosage forms are described below.

A. Coated Core of Modafinil

In one embodiment, an active core of the dosage form of the present invention can include an inert particle such as a commercially available non-pareil sugar sphere. The amount of modafinil in the core will depend upon the dose that is desired. Generally, the core will contain about 5 to 90%, more typically 5 to 60%, by weight, of the drug based on the total weight of the core. Those skilled in the art will be able to select an appropriate amount of modafinil for coating or incorporation into the core to achieve the desired dosage form. Typically, the coated core can include about 5, 10, 25, 50, 75, 100, 125, 150, 175, 200, 225, 250, 275, 300 or about 400 mg of modafinil.

An aqueous or a pharmaceutically acceptable solvent medium may be used for preparing core particles. The type of inert binder that is used to bind the water soluble drug to the inert particle is not critical, but water soluble or alcohol soluble binders are typically used. Binders such as polyvinylpyrrolidone (PVP), carboxyalkylcelluloses, polyethylene oxide, polysaccharides such as dextran, corn starch, hydroxypropyl methylcellulose ("HPMC" under the old monograph nomenclature; the new monograph name is "hypromellose"), hydroxypropylcellulose, may be used by dispersing them in water at a concentration of from about 0.5 to 5 weight %. The modafinil may be present in this coating formulation in the solution form or may be suspended. The drug concentration may vary from about 10 to 30 weight % depending on the viscosity of the coating formulation.

In one embodiment, the active core may be prepared by granulation or by extrusion and spheronization. Modafinil, a binder such as PVP, an optional dissolution rate controlling polymer such as high viscosity HPMC (or "hypromellose"), and optionally other pharmaceutically acceptable excipients (described below) can be blended together in a high shear granulator, such as Fielder® granulator, or a fluid bed granulator, such as Glatt GPCG granulator, and granulated to form agglomerates by adding/spraying a granulating fluid, such as water or alcohol, and dried. The wet mass can be extruded and spheronized to produce spherical particles (beads) using an extruder. In these embodiments, the drug load could be as high as 90% by weight based on the total weight of the extruded or granulated core.

One of the layers of membrane coating on the drug containing particle may include a plasticized enteric polymer while the other layer may include a mixture of a water insoluble polymer and a plasticized water dispersible/enteric polymer wherein the water insoluble polymer and the water dispersible polymer may be present at a weight ratio of 10:1 to 1:1 and typically about 4:1 to 1:1 and the total weight of the coatings is about 15 to 80 weight % and more typically about 20 to 60 weight % based on the total weight of the multiparticulate dosage form.

An optional intermediate acid containing membrane may include an organic acid such as fumaric acid, citric acid, succinic acid, tartaric acid, malic acid, and maleic acid; and a binder such as PVP. It should be noted that water or alcohol soluble polymers are usually used. The weight of this acid coating is about 5 to 20% based on the total weight of the coated beads. The acid in this membrane delays dissolution of the enteric polymer in the inner layer thereby increasing the lag time as well as decreasing the rate of release of the active ingredient from the coated bead. The composition of the outer layer of the polymeric membrane, as well as the individual weights of the inner, intermediate and outer membrane layers can be further optimized to achieve pulsatile release profiles for modafinil based on predicted in vitro/in vivo correlations. Accordingly, the pulsatile release dosage form of the present invention can be optimized to release an amount of modafinil, preferably an effective amount of modafinil, after a predetermined time period and/or at a particular point in the digestive tract of a person to which the dosage form is administered.

Representative examples of enteric polymers useful in the invention include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methamethacrylate copolymers and shellac. These polymers may be used as a dry powder or an aqueous dispersion. Some commercially available materials that may be used are methacrylic acid copolymers sold under the trademark Eudragit (L100, S100, L30D) manufactured by Rhom Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of water insoluble polymers useful in the invention include cellulose derivatives (e.g. ethylcellulose), polyvinyl acetate (Kollicoat SR30D from BASF), neutral copolymers based on ethyl acrylate and methylmethacrylate, copolymers of acrylic and methacrylic acid esters with quaternary ammonium groups, such as Eudragit NE, RS or RS30D, RL or RL30D and the like.

Both enteric and water insoluble polymers used in forming the membranes are usually plasticized. Representative examples of plasticizers that may be used to plasticize the membranes include triacetin, tributyl citrate, triethyl citrate, acetyl tri-n-butyl citrate diethyl phthalate, castor oil, dibutyl sebacate, acetylated monoglycerides and the like or mixtures thereof. The plasticizer may be about 3 to 30 wt. % and more typically about 10 to 25 wt. % based on the polymer. The type of plasticizer and its content depends on the polymer or polymers, and/or the nature of the coating system (e.g., aqueous or solvent based, solution or dispersion based and the total solids).

In general, it is desirable to prime the surface of the particle before applying the pulsatile release membrane coatings or to separate the different membrane layers by applying a thin hydroxypropyl methylcellulose (HPMC or hypromellose) (Opadry Clear®) film. While HPMC (or hypromellose) is typically used, other primers such as hydroxypropylcellulose (HPC) can also be used.

The membrane coatings can be applied to the core using any of the coating techniques commonly used in the pharmaceutical industry, but fluid bed coating is particularly useful.

The present invention also provides a method of manufacturing a timed pulsatile release dosage form which includes the following steps:

1) coating an inert particle such as a non-pareil seed (sugar sphere), with a drug and polymeric binder or preparing a drug containing particle by granulation or/and extrusion/spheronization to form an active drug particle;

2) coating said active drug particle with a plasticized enteric coating which forms a plasticized enteric coated drug particle; and 3) coating said plasticized enteric coated drug particle with a mixture of a water insoluble polymer and an enteric polymer.

In the present invention, the second and third operations can be interchanged and this feature affords an added flexibility in modulating the release profile from the drug particle. Another added flexibility of the present invention is the optional, application of an organic acid (such as fumaric or succinic acid) containing membrane between the second and third coating operations to further modulate the lag time and release profile from the drug particle. Dosage forms incorporating the multicoated drug containing particles in accordance with the invention may take a variety of forms.

In one embodiment, the formulation may employ a single form of the particulate to provide a time-controlled pulsatile release of the drug several hours after oral administration or to target to specific absorption sites. In another embodiment, dosage forms incorporating the multicoated drug containing particles in accordance with the invention can be combined in a composite dosage form with an amount of modafinil suitable for immediate release (e.g., in a gelatin capsule), thereby providing a composite dosage form having both an immediate release portion and time-controlled pulsatile release portion of modafinil.

Because the optional immediate release portion and the modafinil of the coated core can each include about 5, 10, 25, 50, 75, 100, 125, 150, 175, 200, 225, 250, 275, 300 or about 400 mg of modafinil, a coated core dosage form of the present invention can contain about 10 to 800 mg of modafinil.

B. Delayed Extended Release Forms of Modafinil

In yet another embodiment, a dosage form of modafinil capable of providing at least a bi-modal blood profile of modafinil (e.g., the profile shown in FIG. 2) can be provided. In particular, the present invention can include a dosage form, wherein the dosage form contains at least a portion of modafinil suitable for immediate release, and a second amount of modafinil suitable for a delayed extended release.

In such an embodiment, and as shown in FIG. 1, a first portion of modafinil is immediately released, as shown by the vertical bar at hour 1 in FIG. 1. Specifically, during the first hour after administration, a portion of modafinil (e.g., 100 mg as shown in FIG. 1) can be released from a dosage form of the present invention. As also shown in FIG. 1, there is an elapsed time period where substantially no modafinil 1) is released, and/or 2) is capable of entering a subjects bloodstream, and/or 3) is bioavailable from a second portion of administered modafinil, as shown by the absence of dissolution bars at hours 2 and 3 in FIG. 1. However, after about 0 to 3 hours, more preferably after about 4 hours, additional modafinil can be released from a dosage form of the present invention, and the release of the second portion can last for about 3 to 12 hours, or longer, after initial administration.

The release of the second portion of modafinil takes place over an extended period of time, as shown by the vertical bars during hours 4 to 10 in FIG. 1, and typically occurs after a lag time during which no modafinil is released. Accordingly, such dosage forms that can exhibit a delay before the initiation of release of an amount of modafinil, preferably an effective amount of modafinil, are referred to herein as "delayed extended release" dosage forms or compositions. Such a dosage form can be administered alone or in combination with other dosage forms.

Figure 2:
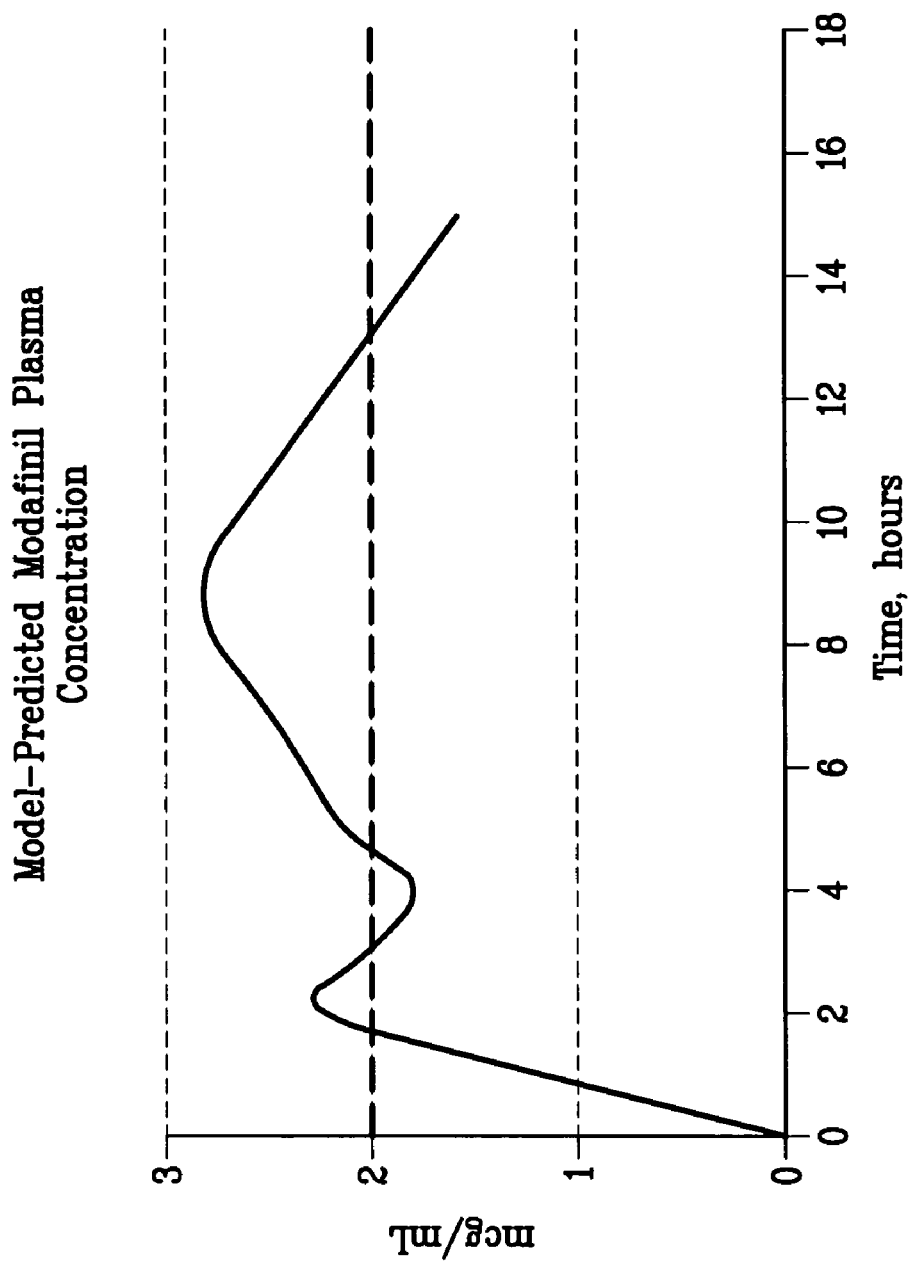
FIG. 2 shows a predicted modafinil blood plasma concentration profile of one embodiment of a delayed extended release dosage form of the present invention.

The effect of such a dosage form or composition of the present invention on blood levels can be described with reference to FIGS. 1 and 2. With respect to modafinil, it is typically desirous for the blood levels of modafinil to increase to at least about 2 µg/ml. This blood concentration can correspond to the amount of modafinil that is bio-available after the immediate release of modafinil in the first hour after administration, as shown in FIG. 1 and described above. However, after about 2 to 4 hours blood levels of modafinil can decrease, and in some instances decrease to below desirable levels, as shown in FIG. 2. The present invention is designed such that the second portion of modafinil can enter the blood stream typically after the immediate release portion of modafinil has been released and in some preferred embodiments after blood levels of modafinil begin to decrease, thereby desirably increasing and/or maintaining blood levels at or above about 2 µg/ml, without the need to administer a second dose of modafinil.

Accordingly, in one embodiment of the present invention, the first portion of modafinil can have an initial pharmacokinetic profile that corresponds substantially to the profile of commercially available forms of modafinil, and in particular Provigil® (modafinil). Thus, the present invention can include about 5, 10, 25, 50, 75, 100, 125, 150, 175, 200, 225, 250, 275, 300 or about 400 mg of modafinil having an immediate release profile.

The immediate release portion can contain modafinil, typically at about 60 to 90% by weight of the immediate release portion. Fillers and other excipients can account for the final weight percent. In a particularly preferred embodiment for use with delayed extended release forms of the present invention, the immediate release portion contains about 79.9% modafinil, 9.9% lactose monohydrate, 5% polyvinylpyrrolidone 90, 5% Ac-Di-Sol® (crosslinked carboxymethylcellulose sodium), and 0.5% magnesium stearate by weight.

In some embodiments, the immediate release modafinil can be the modafinil described in U.S. Pat. No. RE 37,516, the content of which is hereby incorporated by reference. The immediate release formulation can be combined with an amount of a delayed extended release formulation of modafinil, described further below, and then combined in a dosage form such as a gelatin capsule, preferably a hard gelatin capsule, thereby forming a composite dosage form.

The delayed extended release composition of modafinil for used in a dosage form suitable for administration to a patient is hereafter described.

B1. Formulations Suitable for Delayed Extended Release

Certain formulations of modafinil that can exhibit delayed extended release are described in Table 1.

As shown in Table 1, modafinil can be combined with polyalcohols such as mannitol, coagulants such as a Polyox® coagulant and lubricants, such as stearic acid to yield a granulation that can provide a delayed and extended release modafinil composition. In certain embodiments of the present invention, the delayed extended release portion of a dosage form of the present invention can include about 5, 10, 25, 50, 75, 100, 125, 150, 175, 200, 225, 250, 275, 300 or about 400 mg of modafinil. In certain particular embodiments, described in Table 1 below, 100 mg of modafinil can be used, thereby arriving at a total delayed extended release formulation weight of about 150 mg.

TABLE 1

Delayed Extended Formulations

|  | Formula 1 | Formula 2 | Formula 3 | Formula 4 | Formula 5 | Formula 6 | Formula 8 | Formula 9 |
|---|---|---|---|---|---|---|---|---|
| Modafinil | 66.7% | 66.7% | 66.7% | 66.7% | 66.7% | 66.7% | 66.7% | 72.0% |
| Mannitol | 18.3% | 20.3% | 22.3% | 24.3% | 26.3% | 28.3% | 13.0% | 13.0% |
| Polyox ® Coagulant | 13.0% | 11.0% | 9.0% | 7.0% | 5.0% | 3.0% | 13.0% | 13.0% |
| Stearic Acid | 2.0% | 2.0% | 2.0% | 2.0% | 2.0% | 2.0% | 2.0% | 2.0% |
| Avicel ® PH200 | 0% | 0% | 0% | 0% | 0% | 0% | 5.3% | 0% |
| Total | 100.00% | 100.00% | 100.00% | 100.00% | 100.00% | 100.00% | 100.00% | 100.00% |

Figure 3:
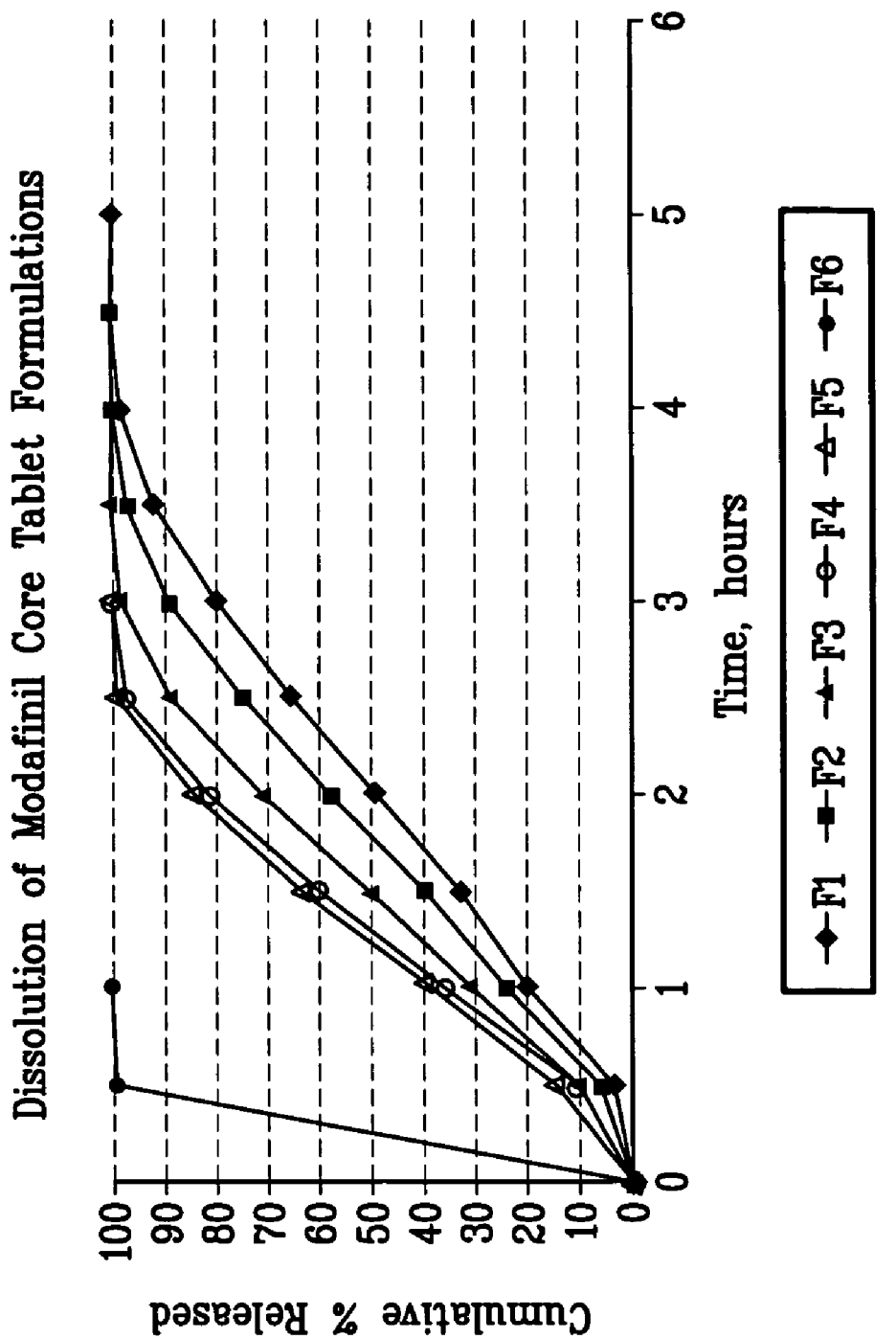
FIG. 3 shows the dissolution profiles of six illustrative formulations of modafinil.
Figure 4:
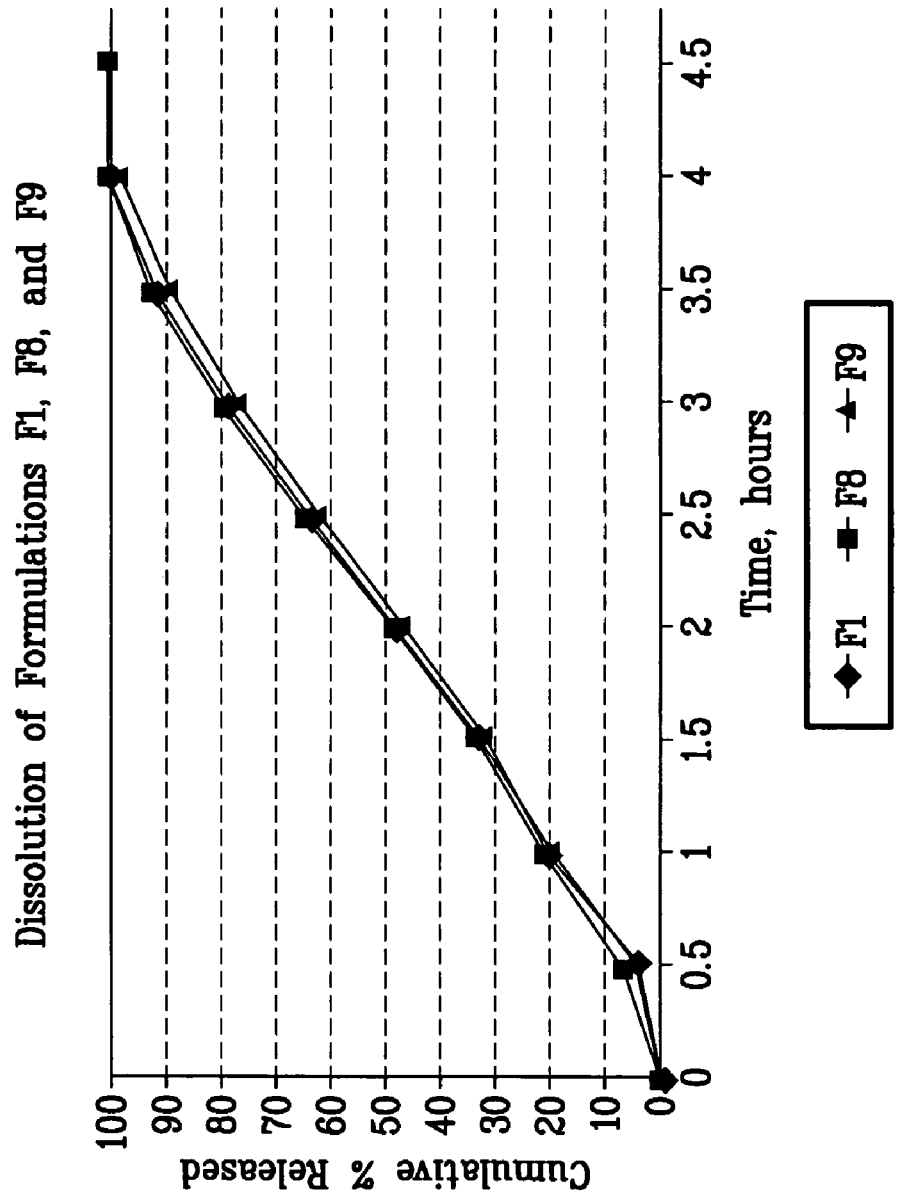
FIG. 4 shows the dissolution profile of three illustrative formulations of modafinil.

Using the formulations described above, caplets, tablets or other dosage forms of the delayed release formulation can be created using standard procedures, including but not limited to encapsulating procedures. However, it should be noted that such dosage forms, without more, typically exhibit "sustained release" blood profiles, i.e., the dosage forms typically immediately release modafinil after ingestion and continue to release modafinil over time, as shown in FIGS. 3 and 4. These compositions can also be formulated into a dosage form, and can exhibit extended release profiles, releasing modafinil for a period of 3 to 12, typically 4 to 12 hours, more typically 6-12 hours after ingestion.

The dosage forms formed from the compositions described in Table 1 can be optionally base coated to seal the tablets for subsequent processing. Suitable sealers include, but are not limited to HPMC (or hypromellose), HPC, PEG and combinations thereof.

Therefore, without more, dosage forms generated from the compositions prepared in accordance to the description set forth above an in Table 1 typically exhibit "sustained release" profiles and can also be used to prepare other modified release dosage forms of modafinil, including but not limited to other dosage forms, including but not limited to the "tablet capsule," "granulation caplet," and the "layered tablet" sustained release dosage forms, which are further described below. However, for purposes of the present invention, it is preferred that compositions of modafinil which are to exhibit delayed extended release should be prepared in accordance with the description set forth above and in Table 1.

As shown by comparing the dissolution of compositions manufactured in accordance with the description set forth in Table 1 (the dissolution was tested in 0.1 N HCl), wherein the dissolution of the compositions over time is set forth in FIGS. 3 and 4, as the weight percent of the polyol increases and the weight percent of coagulant increases, the delay in time before the initial onset of modafinil release also increases. As also shown in FIG. 4, as the amount of modafinil increases and/or the amount of cellulosic (i.e., Avicel PH200) increases, the effect on the release of modafinil can be minimal relative to formulation F1, shown and described in Table 1.

Accordingly, in order to further slow the release of modafinil, and in some embodiments prevent the release of modafinil for a period of time, typically 0.5 to 4 hours after administration, a dosage form of modafinil, and preferably a dosage form having a composition that is set forth in Table 1, can be banded with one or more bands of one or more polymeric materials, as described in more detail below.

B2. Bands of Polymeric Material

In embodiments of the present invention where a dosage form of modafinil is banded, preferably circumferentially banded, the bands of polymeric material can be made of any polymeric material, preferably a relatively insoluble polymeric material, and more preferably one that does not erode or degrade during the dispensing period. Typical insoluble polymerics include the water insoluble polymerics set forth herein above.

In such embodiments, the number of bands, the position of the bands and the thickness of the bands can control the rate of release of modafinil. In the present invention, a space of 0.5, 1.0, 1.5, 2.0, 2.5 or 3.0 mm can be present between bands if multiple bands are used. Each band can be 0.5, 1.0, 1.5 or 2.0 mm wide and have a thickness of about 0.1 to 100 μm, more typically 0.1 to 50 μm, and in some more preferred embodiment 0.1 to 20 μm.

Figure 5:
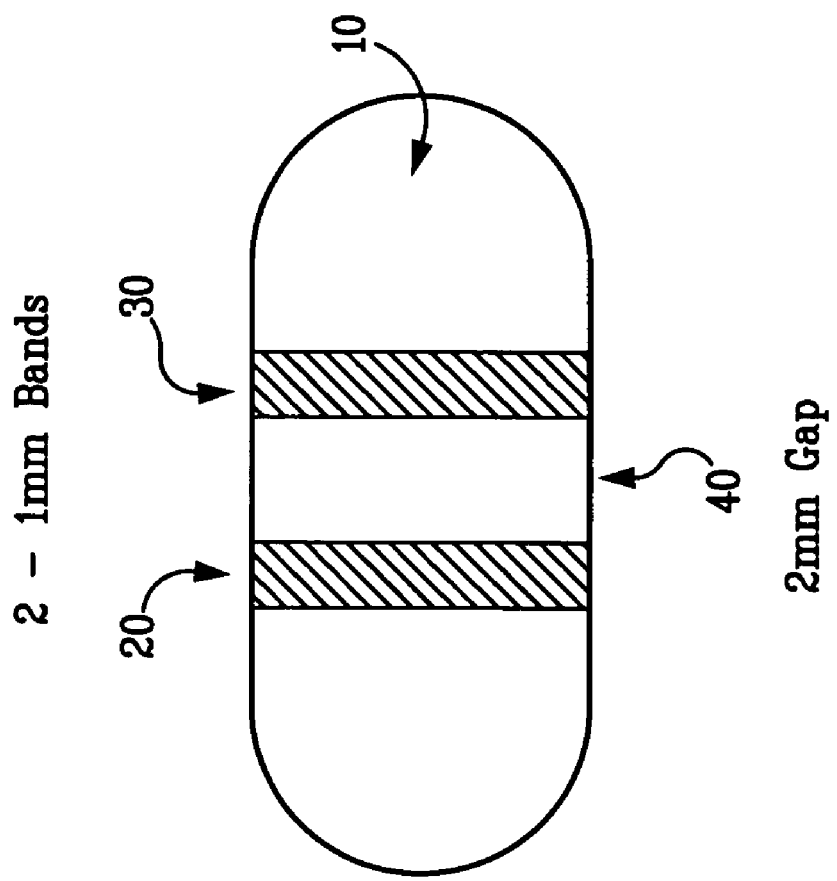
FIG. 5 shows a banded tablet prepared in accordance with the present invention.

As shown in FIG. 5, in one embodiment of the present invention, a caplet formed from formulation F1, described above, has two circumferential polymeric bands thereon. Each band 20 and 30 has a width of about 1 mm and a spacing 40 of about 2 mm therebetween.

Figure 6:
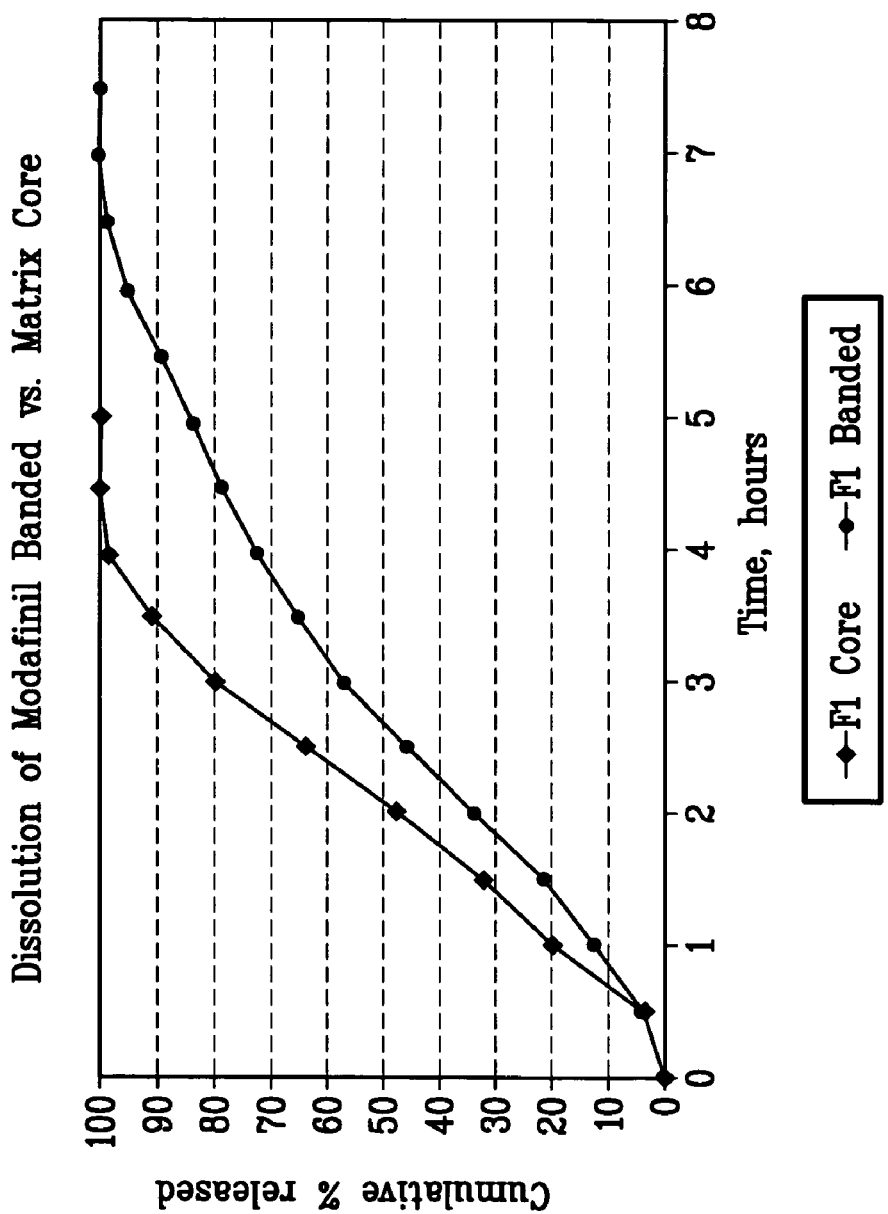
FIG. 6 shows the dissolution profile of an illustrative formulation of modafinil from Table 1 compared to a banded tablet of a formulation of modafinil from Table 1.

Dissolution of the banded caplet was conducted in the same manner as described above (i.e., in 0.1 N HCl). The dissolution of a banded caplet of formulation F1 relative to a caplet of formulation F1 without polymeric bands, is shown in FIG. 6. As shown in FIG. 6, the banded formulation further slows the release of the modafinil and extends the period of time over which modafinil can be released, and/or enter the bloodstream and/or made bioavailable. In some embodiments, the bands can delay the onset of release of modafinil such that there is a lag time (also referred to as a "delay of onset" or "delayed release") during which no modafinil is released. Typically, a delay of onset of modafinil can be from 0 to 4 hours, more typically 0 to 3 hours, more typically 0.5 to 4 hours and in some embodiments 1 to 2 hours, after administration.

To further delay the onset of modafinil from the banded dosage form, the banded dosage form can be optionally coated with a suitable enteric coating. Suitable enteric coatings are readily available to one of skill in the art and include but are not limited to Eudragit L30D-55 and PEG, the suitable coatings set forth with respect to the coated cores of modafinil above, as well as one or more polymers set forth in Table 2 below. The enteric coating may also include other excipients such as talc. The banded dosage form can be coated at a level of about 2 to 10 μg/cm$^2$, typically about 7 μg/cm$^2$. In a preferred embodiment, the enteric coating delays the onset of modafinil such that there is time during which no modafinil is released after administration of the dosage form. Typically, after coating with a suitable enteric coating, delay of onset of modafinil from a coated banded dosage form (e.g., an enteric coated banded caplet) can be from 0.5 to 4 hours, more typically 1 to 2 hours.

Thereafter, in some embodiments of the present invention, an immediate release dose of modafinil, described above, and the enterically coated banded caplet can be combined using conventional procedures into a single composite dosage form (e.g., into a single gelatin capsule). Because the immediate release portion and the delayed extended release portion can each include about 5, 10, 25, 50, 75, 100, 125, 150, 175, 200, 225, 250, 275, 300 or about 400 mg of modafinil, a delayed extended release composite dosage form of the present invention can contain about 10 to 800 mg of modafinil. Such dosage forms can yield blood profiles of modafinil similar to the profile set forth in FIG. 2.

Sustained Release Dosage Forms of Modafinil

In addition to the delayed extended release formulation described above, which can incorporate a type of sustained release formulation, other suitable embodiments of a sustained release formulation of modafinil are hereinafter described. Each of the composite compositions described below include at least an immediate release formulation and a sustained release formulation (described below). Accordingly, in the present invention, dosage form embodiments referred to as "Sustained Release" do not typically exhibit a delay in onset of modafinil, nor do such dosage forms exhibit a significant time period during which no drug is made bioavailable from the dosage form after administration.

In one embodiment, referred to as a "tablet capsule" the present invention can include a capsule containing a first portion of modafinil in a tablet form that is formulated for immediate release and at least a second portion that is in tablet form that is formulated for sustained release.

In another embodiment, referred to as a "granulation caplet" the present invention can include a capsule or caplet containing a first portion of a granulation of modafinil that is formulated for immediate release and at least a second portion that can be in tablet form that is formulated for sustained release.

In yet another embodiment, referred to as "layered tablet" the present invention can include a tablet having two or more layers. In such an embodiment, the tablet can contain modafinil that is formulated for immediate release. This embodiment can also include a second layer of modafinil that is formulated for sustained release.

Each of the above-described embodiments shall be described in more detail below in sections C1 through C3. Further, each of the above described embodiments can contain about 5, 10, 25, 50, 75, 100, 125, 150, 175, 200, 225, 250, 275, 300 or 400 mg, or more, of total modafinil in the first portion (the immediate release portion) and an additional amount of 5, 10, 25, 50, 75, 100, 125, 150, 175, 200, 225, 250, 275, 300 or 400 mg, or more, of modafinil in the second portion. Thus, a composite sustained release dosage form of the present invention can include from about 10 to about 800 mg of modafinil, or more.

C1. Tablet Capsule

In the "Tablet Capsule" embodiment of the present invention, the tablet capsule contains an amount of modafinil suitable for immediate release upon ingestion and at least a second portion of modafinil that can continue to release an amount of modafinil and for up to 6-12 hours after ingestion of the tablet capsule.

In this embodiment of the present invention, at least 50-95% of the modafinil is an immediate release formulation, is in a tablet form, and can be Provigil® (modafinil). Preferably at least about 80% of the tablet capsule includes a composition of modafinil suitable for immediate release. Although the remainder of the tablet capsule embodiment, by weight, can include a sustained release formulation of modafinil detailed above in Table 1 with reference to the "pulsatile release" formulation, preferably the tablet capsule includes a portion of the sustained release formulation of modafinil which is described below in section C4.

The tablet containing the instant release formulation of modafinil and the tablet of the sustained release formulation can be combined in a single dosage form, e.g. a gelatin capsule, in a conventional manner.

C2. Granulation Caplet

One embodiment of the present invention includes a granulation caplet, wherein at least 50-95% of the modafinil is an immediate release formulation and can be a granulation (as distinguished from a tablet) of Provigil® (modafinil). Preferably at least about 80% of the granulation capsule includes a composition of modafinil suitable for immediate release in a granular form, typically contained in a separate caplet. Although the remainder of the granulation caplet embodiment, by weight, can include a sustained release formulation of modafinil detailed above in Table 1 with reference to the "pulsatile release" formulation, preferably the granulation caplet includes a portion of the sustained release formulation of modafinil which is described below in section C4.

The caplet containing the instant release formulation of modafinil and the sustained release formulation can be combined in a single dosage form, e.g. a gelatin capsule, in a conventional manner.

C3. Layered Tablet

In the "Layered Tablet" embodiment of the present invention, the layered tablet contains an amount of modafinil suitable for immediate release upon ingestion and at least a second portion of modafinil that can immediately provide an amount of modafinil for up to 6-12 hours after ingestion of the tablet capsule.

In this embodiment of the present invention, at least 50-95% of the modafinil is an immediate release formulation, and can be Provigil® (modafinil). Preferably at least about 80% of the layered tablet includes a composition of modafinil suitable for immediate release. Although the remainder of the layered tablet embodiment, by weight, can include a sustained release formulation of modafinil detailed above in Table 1 with reference to the "pulsatile release" formulation, preferably the layered tablet includes a portion of the sustained release formulation of modafinil which is described below in section C4.

The two formulations can be combined in a conventional manner, e.g. in a tablet press, such that after processing, the final tabletted dosage form has two or more layers, at least a first layer containing the instant release formulation of modafinil and a second layer containing the sustained release formulation.

C4. Sustained Release Formulation

As noted above, each of the sustained release compositions include an amount of modafinil formulated in such a manner so as to release modafinil over a period of 4 to 12 hours, more typically 6 to 12 hours. Although the formulations described with respect to sustained release can be substituted for the delayed extended release formulations described above and in particular the formulations described in Table 1, and vice-versa, it is preferable that the formulations described in this section herein below be used for the manufacture of sustained release dosage forms of the present invention.

As noted above, a sustained release formulation of the present invention can include an amount of modafinil typically from about 5, 10, 25, 50, 75, 100, 125, 150, 175, 200, 225, 250, 300, or 400 mg. Typically, a sustained release formulation of the present invention further includes at least one suitable polymer, including without limitation one or more of the polymers described in Table 2 below, wherein the weight percents are also described in the far right column in Table 2.

TABLE 2

| Polymer | Type | Level (%) |
|---|---|---|
| Eudraigt | Acrylate-methacrylate polymers | |
| RSPO | Insoluble, High | 10 |
| RLPO | Permeability | |
| NE30D-Suspension* | Insoluble, Low Permeability | 10, 15, 30 |
| | Insoluble, Permeable | 20 |
| Carbopol | Crosslinked polyacrylic acid polymers | |
| 971P | Light cross linking, slow release in SGF | 10, 15 |
| 934P | High cross linking, release through out GIT | 10 |
| 974P | Rigid crosslinking, rapid drug release in SIF | 10, 20 |
| Methocel | Water soluble | |
| K4M* | HPMC, Viscosity: 4000 millipascal-seconds | 15, 18, 30 |
| Methocel:Avicel | Water soluble:Insoluble MCC | 10, 14, 14.5, 15, 16.5, 18, 30 |
| K4M | K4M Viscosity: 4000 millipascal-seconds | 5 |
| K100M | K100M Viscosity: 100000 millipascal-seconds | 10 |
| K15M | | |
| K4M* | K15M Viscosity: 15000 millipascal-seconds | 7, 10, 12 |
| Polyox | Water soluble, Poly (ethylene oxide) polymer | |
| Coagulant | MW: 5,000,000 | 5, 8, 9, 9.5, 10, 20 |
| WSRN301 | | |
| WSRN60K | MW: 4,000,000 | 10, 12.5, 15, 20 |
| | MW: 2,000,000 | 20, 30, 40 |
| Keltone | Alginate Salt | |
| HVCR | High viscosity | 10 |
| Ethyl Cellulose | Water insoluble Ehtylcellulose | |
| Ethocel 100FP | Particle size 40 | 5–15 |

TABLE 2-continued

| Polymer | Type | Level (%) |
|---|---|---|
| Kolidon SR | microns<br>80% Polyvinyl acetate and 19% Povidone, Partly soluble in water | 20 |

It should be noted that the polymers designated with a "*" can be added via wet granulation.

Fillers, including without limitation lactose and dicalcium phosphate and lubricants, including without limitation magnesium stearate.

In some embodiments, modafinil can be at least 20% to 30%, 30% to 60%, or 70% by weight of the sustained release composition. The remainder of the weight of the composition can be the fillers, lubricants and polymers described above. In preferred embodiments, the polymer can be present from 5% to 20% by weight of the sustained release composition, more preferably 7 to 10% or 10 to 16.5%. In a highly preferred embodiment, the polymer is a cellulosic polymer, e.g. Methocel K4M and is present at about 10% by weight. The sustained release formulation can be prepared via direct compression or wet granulation.

Figure 7:
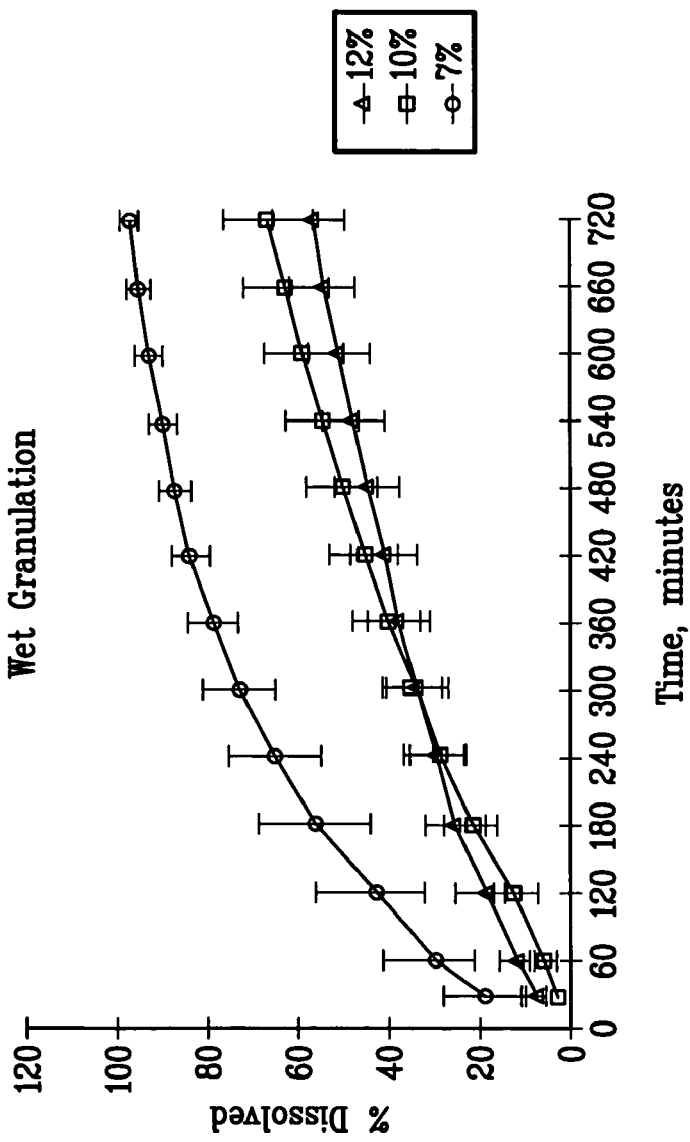
FIG. 7 shows the dissolution profile of illustrative sustained release formulations of modafinil in acid media.
Figure 8:
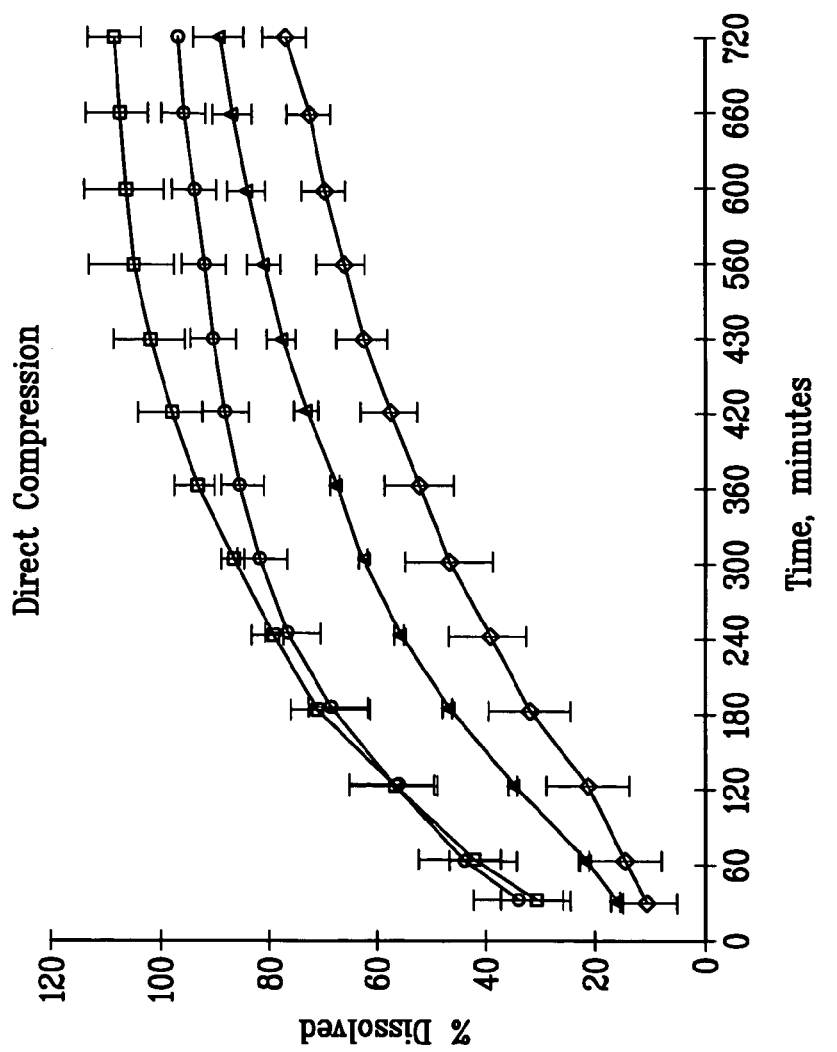
FIG. 8 shows the dissolution profile of illustrative sustained release formulations of modafinil in acid media.

FIGS. 7 and 8 show the dissolution profiles of various sustained release tablets alone. The sustained release tablets were prepared from the sustained release formulation having a total weight of 100 mg of modafinil and a total tablet weight of 250 mg. FIG. 7 shows the dissolution of tablets prepared from direct compression and FIG. 8 shows the dissolution of tablets prepared from wet granulation. Both formulations were prepared in accordance with the teachings herein.

Figure 9:
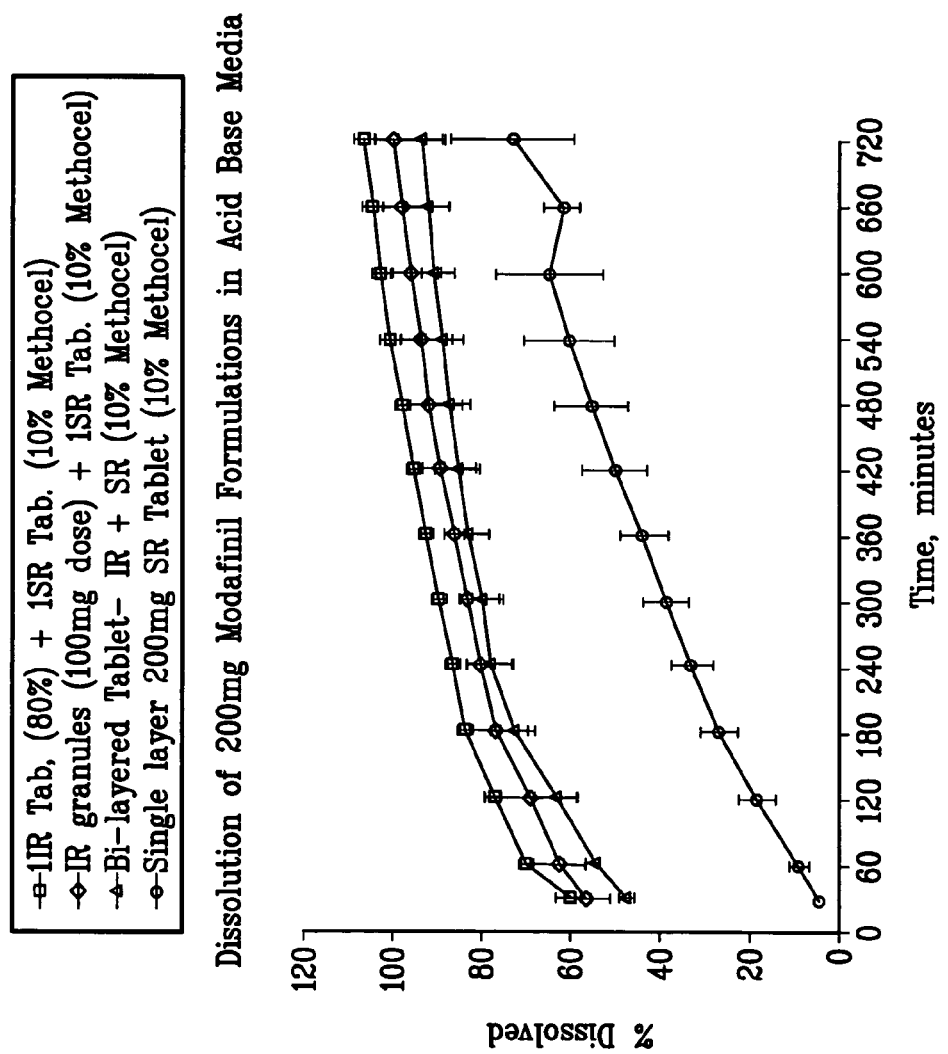
FIG. 9 shows the dissolution profile of a "tablet capsule," "granulation caplet," and the "layered tablet" and a single layer sustained release tablet.

Dissolution profiles of the tablet capsule, granulation tablet, layered tablet and the sustained release formulation used in each, are shown in FIG. 9. The dosage forms incorporated an immediate release portion and a sustained release portion. The sustained release portion contains Methocel K4M as the polymer at 7 to 16.5% by weight of the sustained release portion. As shown in FIG. 9, the tablet capsule embodiment dissolved more quickly in the time period shown, whereas the sustained release formulation alone dissolved the slowest.

Excipients and Other Ingredients

Although the compositions and methods disclosed herein have been described in light of certain embodiments, it is understood that the modafinil dosage forms described herein may be orally administered with an inert diluent or an assimilable edible carrier, for example. The compositions may also be enclosed in a hard or soft shell gelatin capsule, compressed into tablets, or incorporated directly with food of the diet. Such compositions and preparations should contain at least 0.1% of active compound. The percentage of the compositions and preparations may, of course, be varied and may conveniently be between about 2 and about 60% of the weight of the unit.

The tablets, pills, capsules and the like may also contain any of the following: a binder, such as gum tragacanth, acacia, corn starch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring, for example. When the dosage form is a capsule, it can also contain, in addition to materials of the above type, a liquid carrier. Various other materials may be present as coatings or to otherwise modify the physical form of the dosage form. For instance, tablets, pills, or capsules may be coated with shellac, sugar or both. A syrup or elixir may contain the active compounds sucrose as a sweetening agent and methyl and propylparabens as preservatives, a dye and flavoring, such as cherry or orange flavor. Of course, any material used in preparing any dosage form should be pharmaceutically pure and substantially non-toxic in the amounts employed. In addition, the active compounds may be incorporated into sustained-release preparations and formulations.

In some embodiments, disintegrants are added to the formulation to help the all or part of the dosage form disintegrate after consumption, thereby releasing at least a portion of the active ingredients. Some common disintegrants include several modified cellulose derivatives, such as croscarmellose sodium and other modified starch derivatives such as sodium starch glycolate. It will also be understood by one of ordinary skill in the art that other ingredients, binders and lubricants can further affect the dissolution profile of the dosage form.

Further, surfactants, such as ionic, non-ionic and/or bile salt surfactants, can also be included in the present invention. Anionic surfactants include, but are not limited to, sodium alkyl sulfate (Sodium Lauryl Sulphate®) as well as sulfosuccinate derivatives such as docusate sodium. Non-ionic surfactants include, but are not limited to, polyoxyethylene sorbitan fatty acid esters (polysorbates) such as Tween 20®, Tween 80®, Tween 40®, Span 20®, fatty acid esters of polyethylene glycols such as Gelucire 44/14®, Gelucire 50/13®, saturated polyglycolized (including mono, di or tri)glycerides, medium chain monoglycerides (from 6 to 10 carbon atoms long) such as glyceryl monocaprylate (Imwitor 308®), glyceryl monocaproate (Capmul MCM C-8®), glyceryl caprylate/caprate (Capmul MCM®), polyoxyethylene glyceryl caprylate and polyoxyethylene glyceryl caproate (Labrasol®), medium chain fatty acid esters such as glyceryl tri caprate and glyceryltricarilate (Miglyol 612®), block polymers of ethylene oxide and propylene oxide, polyoxyethylene-polyoxyl propylene block copolymers such as Poloxamer 188 (Pluronic F-68®), Poloxamer 237 (Pluronic F-87®), Poloxamer 338 (Pluronic F-108®), Poloxamer 407 (Pluronic F-127®), Poloxamer 124 (Pluronic L-44®), polyoxyl stearate-polyethoxylated (40) stearic acid (Myrj 52®), ethoxylated castor oil-polyethoxylated (60) hydrogenated castor oil (Cremophor EL®), ethoxylated hydrostearic acid polyethylene glycol 660 hydroxystearate (Solutol® HS 15), polyoxyethylene alkyl ethers (from 12 to 18 carbon atoms long) such as polyoxyl 20 cetostearyl ether (Atlas G-3713®), polyoxyl 10 oleyl ether (Brij 96®, Brij 97®, Oleth 10®), polyethylene glycol ether (Triton X-100®, Triton X-114®, Triton X-405®, Triton N-101®) and lecithins such as phospholipids (dimyristoyl DL-alpha-phophatidylcholine). Bile salt surfactants include, but are not limited to deoxycholic acid, sodium deoxycholate, cholic acid, sodium taurocholate.

The compositions and methods of the present invention can also be combined with effective amounts of other pharmaceutical ingredients, including but not limited to pharmaceutical ingredients useful for treating neurological disorders. Suitable pharmaceutical ingredients include antidepressants. Useful antidepressants include but are not limited to tricyclic antidepressants ("TCAs"), Selective Serotonin Reuptake Inhibitors ("SSRIs"), Serotonin and Noradrenaline Reuptake Inhibitors ("SNRIs"), Dopamine Reuptake Inhibitors ("DRIs"), Noradrenaline Reuptake Inhibitors ("NRUs"), Dopamine, Serotonin and Noradrenaline Reuptake Inhibitors ("DSNRIs") Monoamine Oxidase Inhibitors ("MAOIs") including reversible inhibitors of monoamine oxidase type A (RIMAs).

In certain embodiments, a suitable antidepressant can include, but is not limited to, one or more of the following antidepressants: adatanserin hydrochloride; adinazolam; adinazolam mesylate; alaproclate; aletamine hydrochloride; amedalin hydrochloride; amitriptyline hydrochloride; amoxapine; aptazapine maleate; azaloxan fumarate; azepindole; azipramine hydrochloride; bipenarnol hydrochloride; bupropion hydrochloride; butacetin; butriptyline hydrochloride; caroxazone; cartazolate; ciclazindol; cidoxepin hydrochloride; cilobamine mesylate; citalipram; clodazon hydrochloride; clomipramine hydrochloride; cotinine fumarate; cyclindole; cypenamine hydrochloride; cyprolidol hydrochloride; cyproximide; daledalin tosylate; dapoxetine hydrochloride; dazadrol maleate; dazepinil hydrochloride; desipramine hydrochloride; dexamisole; deximafen; dibenzepin hydrochloride; dioxadrol hydrochloride; dothiepin hydrochloride; doxepin hydrochloride; duloxetine hydrochloride; eclanamine maleate; encyprate; etoperidone hydrochloride; fantridone hydrochloride; fehmetozole hydrochloride; fenmetramide; fezolamine fumarate; fluotracen hydrochloride; fluoxetine; fluoxetine hydrochloride; fluparoxan hydrochloride; gamfexine; guanoxyfen sulfate; imafen hydrochloride; imiloxan hydrochloride; imipramine hydrochloride; indeloxazine hydrochloride; intriptyline hydrochloride; iprindole; isocarboxazid; ketipramine fumarate; lofepramine hydrochloride; lortalamine; maprotiline; maprotiline hydrochloride; melitracen hydrochloride; milacemide hydrochloride; minaprine hydrochloride; mirtazapine; moclobemide; modaline sulfate; napactadine hydrochloride; napamezole hydrochloride; nefazodone hydrochloride; nisoxetine; nitrafudam hydrochloride; nomifensine maleate; nortriptyline hydrochloride; octriptyline phosphate; opipramol hydrochloride; oxaprotiline hydrochloride; oxypertine; paroxetine; phenelzine sulfate; pirandamine hydrochloride; pizotyline; pridefine hydrochloride; prolintane hydrochloride; protriptyline hydrochloride; quipazine maleate; rolicyprine; seproxetine hydrochloride; sertraline hydrochloride; sibutramine hydrochloride; sulpiride; suritozole; tametraline hydrochloride; tampramine fumarate; tandamine hydrochloride; thiazesim hydrochloride; thozalinone; tomoxetine hydrochloride; trazodone hydrochloride; trebenzomine hydrochloride; trimipramine; trimipramine maleate; venlafaxine hydrochloride; viloxazine hydrochloride; zimeldine hydrochloride; zometapine.

In certain embodiments, the antidepressant includes citalipram, fluoxetine, fluoxetine hydrochloride, paroxetine, paroxetine hydrochloride, and/or clomipramine hydrochloride, with citalipram, paroxetine, fluoxetine and fluoxetine hydrochloride preferred, with citalipram most preferred.

Other drugs which are useful in treating depressive disorders, e.g., tiagabine, can also be used in combination with the invention.

Formulation and Administration

An appropriate dosage for modafinil is between about 10 mg and about 1000 mg of modafinil, more typically between about 15 mg and 800 mg of modafinil. Particularly useful dosage amounts include, but are not limited to, 100 and 200 mg of modafinil. Preferably, the modafinil has a defined particle size, wherein 95% of the particles are less than or equal to about 200 microns.

The pharmaceutical composition described herein is most preferably administered orally in the form of a vehicle such as a tablet, capsule, powder, pill, liquid/suspension or emulsion. The administration vehicle may comprise a pharmaceutically-acceptable carrier. The carrier may comprise agents that aid solubility, absorption, flavor, color or texture of the vehicle or its contents.

A vehicle of the invention can include + or −10-15% of the modafinil particles, due to factors such as vehicle manufacturing tolerances and expected shelf life of the modafinil. For example, a vehicle labeled as containing 50 mg can be initially prepared with, e.g., 55 or 58 mg of modafinil, with the expectation that after one month to two years of storage, the active amount of modafinil therein has decreased. Vehicles prepared with such adjustments in order to compensate for the expected degradation of the drug fall within the scope of the invention.

Dosage forms of the present invention, the total amount of modafinil can be about 15 mg to about 600 mg, and in other embodiments the total amount of modafinil in the dosage form can be at least about 50 mg to about 600 mg. In preferred embodiments, dosage forms contain 100 mg or 200 mg of modafinil.

In one embodiment, the formulation can contain two or more drug particles with different release characteristics, such as a combination of one or more modified release beads with distinctly different lag times and release rates with or without an immediate release bead to form a timed pulsatile release drug delivery system. Alternatively, a sustained release dosage form can be combined with a pulsatile release dosage form.

Multicoated particulates of two or more drugs can also be combined to obtain synergistic efficacy and enhanced patient compliance.

Methods of Treatment

Although the specific examples presented herein are directed to modafinil of a defined particle size, other uses of modafinil (e.g., for treatment of Parkinson's disease, urinary incontinence, Alzheimer's disorder, ADHD etc.) have been presented in the art, and those utilities are appropriate in conjunction with the invention as disclosed herein.

Accordingly, the present invention also includes a method of altering the somnolent state of a mammal, such as a human, by administering to the mammal an effective amount of modafinil in a composition of the present invention.

Furthermore, the present invention includes a method for enhancing alertness or increasing regularity of sleep rhythms by administering an effective amount of modafinil in a composition of the present invention.

The present invention also includes within its scope a method of treating a mammal diagnosed with a modafinil-responsive disease or condition, including, but not limited to, narcolepsy, sleepiness, excessive sleepiness (e.g., sleepiness associated with disorders of sleep and wakefulness), excessive daytime sleepiness associated with narcolepsy, Parkinson's disease, urinary incontinence, multiple sclerosis fatigue, ADHD, Alzheimer's disorder, sleep apnea, obstructive sleep apnea, depression, and ischemia, by administering an amount of modafinil, as one or more oral unit doses, wherein the unit doses contain an effective amount of modafinil in a composition of the present invention.

Dissolution Testing

As referenced herein, dissolution testing was conducted on tablets from each formulation using a Vankel USP Type III apparatus at 20 dips per minute, and sink conditions were maintained. Samples were taken at 0.5 hour intervals and analysis was conducted using UV spectrophotometrix. FIGS. 7 and 8 show the cumulative percent of modafinil released from each formulation over time.

EXAMPLE 1

100 g batches of each formula set forth in Table 1 were prepared by hand using a low shear ethanol granulation method. The granulations were wet milled through a 16 mesh hand screen, then tray dried at ambient temperature overnight. The dried granulations were dry milled through a 16 mesh hand screen, then dry blended by hand with stearic acid. 150 mg of the final blends, equivalent to 100 mg of modafinil, were manually compressed with a Globe Pharma manual tablet press into 4×12 mm capsule-shaped tablets using 1000 lb compression force. All tablets were base coated to seal the tablets and provide a suitable surface for subsequent banding. The tablets were base coated with HPMC/PEG 8000 (50:50 by weight) using a Vector LDCS 20/30 coating unit.

EXAMPLE 2

Bands were applied circumferentially to the surface of the core tablets of Example 1. Two 1 mm wide bands, spaced 2 mm apart were applied on a single station tablet banding machine using a solution of Eudragit® NE30D containing 8%, by weight, triacetin as a plasticizer. The banding solution also contained a small amount of FD&C Red 40 to allow for visual inspection of the bands. The bands were applied to the surface of each core matrix tablet and allowed to dry at ambient temperature overnight.

Following drying, the banded tablets were top coated to seal the surface and reduce the tackiness of the bands. The tablets were top coated with HPMC/PEG 8000 (50:50 by weight).

EXAMPLE 3

The banded tablets were coated with an enteric polymer to provide the appropriate delay in onset of release (approximately two hours). The banded tablets were coated with Eudragit® L30-55/PEG 8000/talc (84:8:8 by weight) using a Vector LDCS 20/30 coating unit.

EXAMPLE 4

The formulation for the immediate release portion of modafinil can be obtained from Cephalon, Inc under the name Provigil® (modafinil). For use with the banded tablets, the immediate release portion was prepared by low shear aqueous granulation using a Hobart planetary mixer. The granulation was tray dried in a forced air oven at 50 degrees C. to a moisture content of less than 2%. The dried granulation was milled through a 40 mesh screen using an Erweka oscillating mill, then dry blended with magnesium stearate using a Patterson-Kelly V-blender.

EXAMPLE 5

An amount of the immediate release formulation of Example 4 was combined with an enteric coated banded tablet of Example 3 in a size #1 gelatin capsule to provide a composite dosage form exhibiting a bi-modal release profile of modafinil, wherein the immediate release portion was release from the dosage form and made bioavailable, which was followed by a period of time wherein substantially no additional modafinil was released and made bioavailable. After a period of about 2 hours, additional modafinil was released and made bioavailable.

EXAMPLE 6

For a sustained release formulation prepared by direct compression, modafinil, polymer and filler were added to a Turbula Mixer for 10 to 20 minutes. Lubricant was added and mixed for an additional 5 minutes. The mixture was then compressed on a Manesty Beta Press, with round tooling at 9.5 mm, to form tablets having a total weight of 250 mg, wherein 100 mg of the total tablet weight was modafinil.

EXAMPLE 7

For a sustained release formulation prepared by wet granulation, modafinil, polymer, filler were added to a Erweka mixer for 5 to 20 minutes. Granulation fluid was then added to the mixer and was mixed for an additional 5 minutes. The mixture was then dried in a Blue M electric oven at 40 degrees C. until the moisture level was less than or equal to 1.5%. The dried mixture was then passed through a Erweka mixer fitted with a 16 mesh screen. The dried mixture and magnesium stearate were then combined in a Turbula mixer and mixed for 5 minutes. The mixture was then compressed on a Manesty Beta Press, with round tooling at 9.5 mm, to form tablets having a total weight of 250 mg, wherein 100 mg of the total tablet weight was modafinil.

Definitions "Particle," as used herein, refers to an aggregated physical unit of the acetamide compound, i.e., a piece or a grain of acetamide.

As used herein, "about" means plus or minus ten percent of the indicated value, such that "about 20 mg" indicates 18 to 22 mg.

As used herein, "consisting essentially of" refers to excluding other active ingredients but including excipients and additional amounts of the active ingredient to account for degradation or otherwise.

An "effective amount," as used herein, is an amount of modafinil that is effective for treating a somnolent or somnolescent state, i.e., an amount of modafinil that is able to reduce or eliminate the symptoms of a somnolescent state. An effective amount of a pharmaceutical composition of the invention is useful for enhancing alertness, or increasing regularity of sleep rhythms and treat other disorders described herein.

A "pharmaceutical composition," as used herein, means a medicament for use in treating a mammal that comprises modafinil prepared in a manner that is appropriate for administration to a mammal. A pharmaceutical composition according to the invention may also, but does not of necessity, include a non-toxic pharmaceutically acceptable carrier. A pharmaceutical composition can also include bulk active modafinil for use in preparing dosage forms.

"Controlled drug delivery" refers to a pre-designed release of a bulk material.

"First order release" refers to drug release that changes depending upon the rate constant and concentration, i.e., the amount of drug released in a given time period depends on how much drug is in the dosage form.

"Zero-order release" refers to drug release which proceeds at a constant rate until the amount of the drug in the dosage form is depleted, i.e., the same amount of drug will disappear in a given amount of time, regardless of how much drug is present.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations. Further, the contents of all references cited herein are hereby incorporated by reference.

What is claimed is:

1. A pharmaceutical composition in unit dose form, wherein upon administration to a patient, the composition releases two or more amounts of a modafinil compound, comprising:
   a) a core particle comprising an effective amount of a modafinil compound;
   b) a first membrane comprising a water-insoluble polymer applied in at least 2 circumferential bands;
   c) a second membrane comprising an enteric polymer; wherein the core particle is coated with the first and second membranes to form an active drug particle; and
   d) an immediate release formulation of a modafinil compound; wherein no substantial release of the modafinil compound from the active drug particle occurs until about three to six hours after administration.

2. The pharmaceutical composition of claim 1 wherein the core particle comprises the modafinil compound and a polymeric binder.

3. The pharmaceutical composition of claim 1 wherein the core particle is prepared by precipitation, granulation and milling, or extrusion/spheronization.

4. The pharmaceutical composition of claim 1 wherein the enteric polymers are each independently selected from the group consisting of esters of cellulose, polyvinyl acetate phthalate, pH sensitive methacrylic-methylmethacrylate copolymers and shellac.

5. The pharmaceutical composition of claim wherein the water insoluble polymer is selected from the group consisting of ethylcellulose; polyvinyl acetate; neutral copolymers based on ethyl acrylate and methylmethacrylate; and copolymers of acrylic and methacrylic acid esters having quaternary ammonium groups.

6. The pharmaceutical composition of claim 1 wherein at least one of the membranes further comprises a plasticizer.

7. The pharmaceutical composition of claim 6 wherein the plasticizer is selected from the group consisting of triacetin, tri-butyl citrate, tri-ethyl citrate, acetyl tri-n-butyl citrate, diethyl phthalate, castor oil, dibutyl sebacate, acetylated monoglycerides and mixtures thereof.

8. The pharmaceutical composition of claim 1 wherein the second membrane has sufficient thickness to prevent substantial release of the modafinil compound for a period of three to six hours after oral administration to a patient.

9. The pharmaceutical composition of claim 1 wherein the unit dose form is a capsule.

10. The pharmaceutical composition of claim 9 wherein the capsule is a hard gelatin capsule.

11. The pharmaceutical composition of claim 9 wherein the capsule comprises a single form of the active drug particle such that the composition provides for a time-controlled pulsatile release of the modafinil compound upon oral administration to a patient.

12. The pharmaceutical composition of claim 11 wherein the modafinil compound is released from the active drug particle three to six hours after oral administration to a patient.

13. The pharmaceutical composition of claim 9 wherein the capsule comprises two or more active drug particles with different release times.

14. The pharmaceutical composition of claim 1 wherein the active drug particle comprises a delayed extended release formulation of a modafinil compound.

15. The pharmaceutical composition of claim 14 wherein the amount of modafinil compound in the immediate release formulation is 60 to 90 percent by weight of the immediate release formulation.

16. The pharmaceutical composition of claim 15 wherein the immediate release formulation comprises about 79.9% racemic modafinil, about 9.9% lactose monohydrate, about 5% polyvinylpyrrolidone 90, about 5% crosslinked carboxymethylcellulose sodium, and about 0.5% magnesium stearate by weight.

17. The pharmaceutical composition of claim 1 wherein the blood profile of a patient to whom the composition was administered corresponds substantially to the profile set forth in FIG. 2.

18. The pharmaceutical composition of claim 1, further comprising an effective amount of an antidepressant.

19. The pharmaceutical composition of claim 1, 11, or 14 wherein the modafinil compound is racemic modafinil.

20. The pharmaceutical composition of claim 1, 11, or 14 wherein the modafinil compound is the levorotatory form of modafinil.

21. The pharmaceutical composition of claim 1 or 14, wherein the total amount of modafinil compound contained within the dosage form comprises 10 to 800 mg of racemic modafinil.

22. The pharmaceutical composition of claim 9 wherein the capsule comprises a composite dosage form that provides for a time-controlled pulsatile release of the modafinil compound upon oral administration to a patient.

* * * * *